United States Patent [19]

Murdoch et al.

[11] Patent Number: 4,719,246
[45] Date of Patent: Jan. 12, 1988

[54] POLYLACTIDE COMPOSITIONS

[75] Inventors: Joseph R. Murdoch, Wilmington, Del.; Gary L. Loomis, Drexel Hill, Pa.

[73] Assignee: E. I. Du Pont de Nemours and Company, Wilmington, Del.

[21] Appl. No.: 944,588

[22] Filed: Dec. 22, 1986

[51] Int. Cl.⁴ ............................................... C08J 9/28
[52] U.S. Cl. ...................................... 521/134; 521/64; 521/182; 521/189; 525/410; 525/413; 525/415; 528/354

[58] Field of Search ............... 521/134, 182, 189, 64; 528/354; 525/410, 413, 415

[56] References Cited

U.S. PATENT DOCUMENTS 4,471,077  9/1984  Lange ..................... 521/56

Primary Examiner—Morton Foelak

[57] ABSTRACT

Novel polylactide composition containing segments of poly(R-lactide) interlocked with segments of poly(S-lactide).

16 Claims, No Drawings

POLYLACTIDE COMPOSITIONS

BACKGROUND OF THE INVENTION

This invention relates to novel polylactide compositions e.g., to polymers containing segments of poly(R-lactides) interlocked with segments poly(S-lactides) and to their preparation in various forms.

The optionally active enantiomers L-lactic acid (S-lactic acid) and D-lactic acid (R-lactic acid), and the corresponding cyclic diesters thereof, L- and D-(S- and L-)lactides, are known as are methods of polymerizing the enantiomeric acids or, preferably for high molecular weight, their lactides, to the enantiomeric open-chain polymers herein referred to as poly(R-lactide) and poly(S-lactide), respectively, using mainly cationic initiators, e.g. by compounds of tin, antimony, lead, zinc. C. Lavallee et al., Proc. Int. Symp. on Adv. in Polymer Syn., Aug. 26–31, 1984, Plenum 1985, pp 441-461 discuss preparation and properties of racemic and optically active substituted poly(beta-propiolactones). Blends of these poly-R- and poly-S-lactones (1:1) were reported to form a "stereocomplex" having a crystalline melting point of 203° C. as compared to 164° C. for the individual isotactic enantiomers, and a different crystal structure and morphology. Binary mixtures containing an excess of either enantiomer also contained the high-melting phase. The authors describe poly(L-lactide) and poly(D-lactide) as being highly crystalline, melting at about 180° C., whereas poly(D,L-lactide) is amorphous. Blends of the individual poly(lactide)enantiomers were not mentioned. Racemic polylactides, prepared from racemic monomers by these methods, are either amorphous or somewhat crystalline, melting at about 130° to 140° C., while the polymers prepared from pure enantiomeric monomers are optically active, isotactic and crystalline, melting in the range of about 145° to 215° C. Copolymers of the enantiomeric lactides are reportedly crystalline only when over 90% of one enantiomer is present; melting point decreases from about 173° to 124° C. as composition changes from pure enantiomer to 8% comonomer (opposite enantiomer). Polylactide enantiomers are used in various surgical and pharmaceutical applications, including sutures and other prosthetic parts, and as controlled-release encapsulants for biologically active materials such as anticancer agents and other drugs.

B. Kalb et al., Polymer 21, 607 (1980) describe the crystallization behavior of poly(L-lactide) prepared by cationic ring-opening polymerization of the dilactide. The polymer, described as bioabsorbable, biodegradable and biocompatible, was found to have an equilibrium melting point of about 215° C., a Tg of about 55° C. and a viscosity average molecular weight of about 550,000 measured in chloroform. Precipitation of poly(L-lactide) from chloroform solution with a mixture of glycerol and ethanol produced porous fibers having pores of 0.1 to 0.6 micron diameter.

D. L. Wise et al. in "Drug Carriers in Biology and Medicine", Ed. G. Gregoriadis; Acad, Press, N.Y., 237–270 (1979) discusses the polymerization of D- and L-lactic acids and the dilactides thereof, the former providing only low molecular weight polymers. Preparation of high molecular weight polymers from D-, L- and D,L-lactides using organometallic catalysts such as alkyl zinc, aluminum or tin is described. Polymers from the individual enantiomeric lactides are preferred over those from the racemate because sutures prepared therefrom by melt or solution spinning exhibit less shrinkage. Copolymers of dilactide and glycolide and their use in various biomedical applications are also described.

U.S. Pat. No. 4,471,077 discloses that microporous powders can be prepared from a polymer of D,L-lactic acid, D(−)lactic acid, L(+)lactic acid, or a copolymer thereof with another hydroxycarboxylic acid. Porous powder is prepared by cooling a solution of polymer (poly-D-lactide is exemplified) in hot xylene, filtering off the precipitated polymer and vacuum-drying. The exemplified powder had "interconnecting pores", 55% pore volume, and particle sizes largely in the range 100–400 microns. The powders can be formulated with medicants, nutrients, plant growth regulators, fragrances and the like, for controlled dispensation. Although the patent teaches that the polymers can be mixed, no examples or advantages are ascribed to the mixtures in any proportions.

Ring-opening polymerizations of other lactones or heterocyclic monomers, e.g. of beta-propiolactones, alkylene oxides and alkylene sulfides, are known, initiated by ionic or coordination compounds some of which are stereoselective and, in certain cases, avoid racemization of optically active monomers during polymerization. Certain polymers prepared from racemic monomers using stereoselective initiation are reportedly optically active, indicating polymerization of only one enantiomer. D. Grenier et al. J. Poly. Sci. Poly. Phys. Ed., 22, 577 (1984); ibid. 19, 1781 (1981); Macromolecules, 16, 302 (1983) disclose the preparation of D-(R+) and L-(S−)enantiomers of poly(alpha-methyl-alpha-ethyl-beta-propiolactone) by ring-opening polymerization of the corresponding enantiomeric, and preparation of the racemic polymer from the racemic lactone. Blends of the polymeric enantiomers were prepared in solution and blend properties were compared with those of the individual polymers. The latter each had a crystalline melting point of about 160° C., while approximately 1:1 (ee equal or less than 0.5) blends all melted at about 202° C. Blends having higher enantiomeric excesses showed two melting points at about 202° and 160° C. respectively. The so-called higher melting complex was shown to have a different morphology and different physical properties to the individual polymeric enantiomers.

K. Hatada et al. Polymer J., 13 (8), 811 (1981) disclose 1:1 blends of R- and S-enantiomers of poly(methylbenzyl methacrylate) which were distinctly crystalline, melting at 228°–230° C.; the individual enantiomeric polymers had little or no crystallinity and liquified below about 160° C.

H. Matsubayashi et al., Macromolecules 10, 996 (1977); P. Sumas et al., Die Makromol. Chem., 156, 55 (1972) disclose preparation of optically active and racemic poly(t-butylethylene sulfide) by polymerization of optically active and racemic monomers, respectively, using a stereospecific initiator. The racemic and active polymers had crystalline melting points of 210° C. and 162° C. respectively, and different crystal structures and morphology.

H. Sakakihara et al., Macromolecules 2, (5), 515 (1969) disclose preparation of racemic and optically active poly(propylene sulfides), the former by sterospecific initiation. X-ray diffraction studies led to the conclusion that the crystal structures of both racemic and optically active polymers were the same.

It is known that the melting points of enantiomers of a given compound are the same and that progressive addition of one enantiomer to the other generally causes a drop in melting point. Usually a minimum (eutectic) melting point is reached, the melting point rising with further addition of the second enantiomer. In some instances, including the classical case of D- and L-tartaric acids, a maximum melt point is reached at approximately the 1:1 composition. This maximum may be higher or lower than that of the individual enantiomers, and in either case is thought to reflect a new crystalline phase ("molecular compound" of the D- and L-forms). In other instances no maximum is obtained. There is no reliable way to predict the behavior of enantiomeric pairs in non-polymers let alone in polymers whose crystalline phases, if any, are more complex.

The art discloses preparation of selected enantiomeric poly(alkylene sulfides), poly(alkylene oxides), poly(methylbenzylmethacrylates), and beta-propiolactones. Poly(methylethylene sulfides) prepared from racemic monomer or from an enantiomer by stereoselective coordination polymerization both melt at about 60° C. but enantiomeric and racemic polymers of t-butylethylene sulfide, prepared with the same catalyst are both crystalline, melting at about 160° and 205° C. respectively. The high-melting racemic polymers reportedly are mixtures of D- and L-enantiomers. Racemic poly(t-butylethylene sulfide) prepared from racemic monomer with ionic catalysts is amorphous. Enantiomers of poly(methylbenzyl methacrylates) prepared from enantiomeric monomers are essentially amorphous, but 1:1 blends of the polymeric enantiomers form a highly crystalline "complex" melting at 228°-230° C.

Ring-opening polymerization of beta-propiolactones, especially beta methyl- or trifluoromethyl beta-propiolactone, has been studied in detail. Coordination polymerization of enantiomeric monomers produces isotactic, enantiomeric polymers melting at 164° C. Blends (1:1) of these enantiomers melt at about 203° C. and differ in crystal morphology and structure from the component polymers. Moreover, the new phase persists in blends containing enantiomeric excesses of as high as 1:45. Formation of a (high melting) complex is reportedly not always the result of mixing isotactic enantiomeric polymers; equimolar mixtures of isotactic enantiomeric polymers of beta-butyrolactam, propylene oxide or methylthiirane (methyl ethylene sulfide) show the same thermal properties and crystalline structure as the corresponding individual polymers.

U.S. Pat. No. 3,797,499 (1974) discloses absorbable surgical sutures prepared from poly(L-lactide) or copolymers of L-lactide and glycolide of high tensile strength and hydrolytic behavior and absorbability. The poly-L-enantiomer is preferred because of availability and higher melting point.

D. K. Gilding et al. Polymer 20, 1459 (1979) report the preparation of poly(L-lactide), poly(D,L-lactide) and copolymers of glycolide and lactide using antimony, zinc, lead or tin catalysts, preferably stannous octanoate. Poly(L-lactide) was about 37% crystalline and the poly(D,L-lactide) was amorphous. U.S. Pat. No. 4,279,249 discloses bioabsorbable prosthesis (osteosynthisis) parts preparable from poly-D- or poly-L-lactic acid having enantiomeric purity of over 90%. The latter had a crystalline melting point of 175° C.

U.S. Pat. No. 4,419,340 discloses controlled release of anticancer agents from biodegradable polymers including polymers of L(+)-, D(−)- and D,L-lactic acids and copolymers thereof. U.S. Pat. No. 3,636,956 discloses absorbable sutures prepared from enantiomeric poly(lactides), poly(D,L-lactide) and copolymers. Melting point, tensile strength are reported higher from the individual enantiomeric poly(lactides). D. L. Wise et al., J. Pharm. Pharmac., 30, 686 (1978) describe sustained release of antimalarial drugs from poly-L(+)lactide or copolymers thereof with D,L-lactide or glycolide.

The preparation of high molecular weight poly-D- and poly-L-lactides and mixtures thereof in the proportions 1–99 to 99–1, formation of a high-melting phase in the blends, and various medical uses, including surgical thread, artificial ligaments and the like, are disclosed in Japanese Unexamined Application J61/036-321.

As discussed hereinabove, poly(lactides) have many desirable properties for biological applications, but use of even the crystalline enantiomeric poly(lactides) is limited by melting point, hydrolysis rate, sensitivity to solvents, polymeric strength and the like which, while superior to the racemic polylactide, are marginal or inadequate for many applications.

M. Goodman et al., Polymer Letters 5, 515 (1967) describe synthesis of optically active, highly crystalline poly(lactide) from optically pure S(+)lactic acid via the lactide. Solution properties of the polymer dissolved in chloroform, acetonitrile, trifluoroethanol and trifluoroacetic acid were studied.

Fieser & Fieser "Organic Chemistry", 3rd Ed. Reinhold 1956, pp 267–269 describe non-polymeric optically active compounds and the melting behavior of mixtures of opposite enantiomers, including the formation of a "D,L-compound" which may melt higher or lower than the individual enantiomers, depending on their chemical nature, but always higher than the eutectic melting point formed by adding one enantiomer to its opposite enantiomer.

SUMMARY OF THE INVENTION

The invention comprises compositions wherein segments of poly(R-lactide) interlock or interact with segments of poly(S-lactide). The segments can be present in mono- or copolymers including random, block and graft copolymers so long as the segments are arranged to permit at least some interlocking or interacting. The segments can be present in the molar ratio of 99:1 to 1:99, preferably about 1:9 to about 9:1, more preferably about 1:1. Compositions comprising at least one homopoly(lactide) are preferred. Epsilon-caprolactone is a preferred comonomer. The segmental interlocking can produce a novel crystalline phase which has a crystalline melting point higher than that of either component. In preferred compositions this phase accounts for most of the total crystallinity.

Compositions in the form of gels, porous structures, composits, shaped articles, solutions, coatings and coated substrates are within the perview of the present invention.

The present invention includes processes for preparing the above described compositions e.g., by mixing and combining the previously-prepared polymeric components in a suitable solvent or in the molten state, and processes for preparing gels and porous structures of the compositions.

The invention can be employed to prepare absorbable stitching threads used in vivo, bone plates, artificial tendons, artificial ligaments, artificial blood vessels, time release carriers for medication, films used in cultivation in agriculture, fibers, ropes, time release carriers for agrichemicals, and separatory films for industrial use.

DETAILED DESCRIPTION OF THE INVENTION

Optically active R- and S-enantiomers of lactic acid and of the lactides are commercially available and can be homopolymerized or copolymerized by known methods such as bulk (co)polymerization usually in a dry, inert atmosphere with an ionic catalyst such as stannous octanoate. The resultant enantiomeric poly(lactides), after purification e.g., by precipitation from solution in a suitable solvent such as methylene chloride or chloroform by addition of a non-solvent such as diethyl ether, have crystalline melting points of 173° to 177° C. Lactide copolymers will generally have lower crystalline melting points, depending on lactide content but may be amorphous. It should be understood that the term "copolymers" as used herein includes polymers prepared from mixtures of R- and S-lactide as well as from R- or S-lactide and at least one non-lactide comonomer. Examples of suitable non-lactide comonomers include those capable of condensation polymerization with lactide or lactic acid, i.e., lactones such as epsilon-caprolactone, beta-propiolactone, alpha,alpha-dimethyl-beta-propiolactone, delta-valerolactone, alpha-, beta- or gamma-methyl-epsilon-caprolactone, 3,3,5-trimethyl-epsilon-caprolactone, dodecanolactone; lactams; other hydroxy acids such as glycolic acid; amino acids and the like. Operable copolymers will in general contain blocks of lactide of sufficient length such that the copolymer exhibits a crystalline melting transition characteristic of lactide, although enantiomerically balanced compositions of certain amorphous lactide copolymers may also exhibit a crystalline melting transition, reflecting the novel phase. Especially useful thermoplastic elastomeric compositions are comprised of two block copolymers containing, respectively, lactide blocks of opposite enantiomeric configuration and "soft" blocks of polyether, polyester or other similar polymer. The present composition can contain non-lactide polymers, fillers and other known additives.

The segments of poly(R-lactide) in the polymers of this invention are interlocked with segments of poly(S-lactide). Interlocked or interlocking as used herein means the mutual restraint of independent motion exerted by one of the polylactide segments on the oppositely configured segment. In this sense, the segments interact or can be considered interacting, but not so tightly bound as compared to polymer chains which are cross-linked. X-ray diffraction indicates that when interlocked the interchain distance of the interlocked portion of the poly(lactide) chain or segment is less than the interchain distance of the separate (unlocked) poly(-lactide) chains. Only a portion of the polymer segments need be interlocked to realize the benefits of the present invention, i.e., the poly(R-lactide) and/or the poly(S-lactide) can be part of a block copolymer or be present as recurring segments in a random copolymer it being understood that the level of interlocking will significantly decrease in later case at least because the (R- and S-) units are less likely to coincide and thereby provide sites for potential interlocking or interaction. Branching may also interfere with interlocking. The interlocking is evidenced for example by the creation of a high melting phase and a distinctive X-ray diffraction i.e., a reduced layer line spacing consistent with a tighter helix and altered cell dimensions relative to the individual unlocked segments.

Compositions of the invention can be prepared by several methods including dissolving appropriate pairs of enantiomeric homopolymers and/or copolymers in the desired enantiomeric ratio in a suitable solvent such as methylene chloride or chloroform at a concentration of at least about 1 wt%, preferably about 10 wt% to about 20 wt%, with agitation, at a temperature within the liquid or fluid range of the solvent e.g., −100° to 300° C., preferably 10°–100° C., at sub to superatmospheric pressures, followed by evaporation of the solvent. Preferably the individual enantiomers are dissolved separately and the solutions mixed together with agitation until homogeneous. Suitable solvents for preparing the compositions of the invention include chlorinated solvents such as chloroform, methylene chloride and chlorinated ethanes, sulfolane, N-methylpyrrolidone, dimethylformamide, tetrahydrofuran, butyrolactone, trioxane and hexafluoroisopropanol.

Alternatively, the enantiomeric lactide polymers may be mixed in the molten state. The molten composition can be extended and quenched into molding powder of usual dimensions or processed into finished objects by methods known in the art e.g., by injection molding. More particularly, the dissolved or molten compositions can be cast or extruded onto a suitable substrate or mold and recovered as film, shaped object, or (from solution) a gel.

Gels may form spontaneously from a solution containing at least 1 wt% of blended poly(lactide) enantiomers, preferably at least 5 wt%, on stirring at about 15° to about 30° C., preferably room temperature. The lower concentration limit for gelation depends on the solvent employed. The rate of formation of gel generally increases with increasing polymer concentration, polymer molecular weight, agitation rate and decreasing enantiomeric excess. Temperatures significantly above 30° C. or below the 15° C. may reduce the gelation rate. Gel formation is believed to reflect reduced solubility of the high-melting cyrstalline phase. The gels can be re-dissolved in high-boiling solvents at temperatures above about 80°, indicating that they are not covalently cross-linked.

Interlocked homopoly(lactides) normally exhibit two crystalline melting transitions in differential scanning calorimetry (DSC) while those containing one or more copolymers may exhibit three or more crystalline melting transitions. The lower-melting transitions occur at temperatures essentially equivalent to melting transitions in the individual component polymers, and reflect lower-melting crystalline phases characteristic of the component polymers. The high-melting transition, which occurs at about 40° to about 60° above the highest of the lower transitions, reflects the aforementioned novel high-melting crystalline phase, also herein referred to as "high-melting phase", and which is further characterized by a unique X-ray diffraction pattern and physical properties.

The relative amounts of high- and low-melting phases present in the invention compositions are determined, in part, by lactide enantiomeric balance, i.e. the relative molar amounts of R- and S-lactide segments present, and, in part by the thermal history of the compositions. The proportions of high- and low-melting phases can be estimated from the areas under the respective DSC endotherms. Brief melting of the invention compositions, followed by quenching to below room temperature, results in an increase of the proportion of high-melting phase present. In compositions wherein the opposite enantiomeric lactide segments are approximately balanced, i.e. the relative molar amounts of R- and S-lactide segments are approximately equal, this thermal treatment can result in the high-melting phase accounting for essentially all of the crystallinity present.

The proportion of high-melting phase can be reduced by heating the compositions for extended periods e.g., several hours at a temperature of about 10° to about 30° above the highest crystalline melting point, followed by slow cooling to room temperature. Rapid quenching from the molten state can also result in an increased amount of amorphous polymer that exhibits no crystalline melting transition. By careful selection of enantiomeric balance and thermal treatment, desired proportions of high- and low-melting crystalline phases and amorphous content can be "tailored" to achieve a desired balance of properties for selected uses. Compositions wherein the crystallinity is derived mainly from the high-melting phase, such as those prepared via gelation, are preferred. In view of the foregoing, it should now be apparent that some of the conditions employed in melt-processing can significantly alter the proportion of high-melting phase.

It has also been found that the polymers in the composition can differ in molecular weight by a factor of at least 3 without departing from the present invention.

As previously mentioned and as demonstrated in the examples, the presence of high-melting crystalline phase substantially increases certain physical properties such as tensile strength, toughness, tensile elongation, hydrolytic stability and thermal stability while desirable biochemical properties and biocompatibility are retained. These applications, which are well described in the art, frequently require tough, durable, strong polymer, for example in prosthetic devices, and accordingly benefit from the present compositions wherein these properties are substantially enhanced. Alternatively, the present high-melting, higher-performance compositions permit greater dilution with lower-cost compatible polymers such as poly(glycolic acid) without expressive compromise in desired physical properties.

Lactide-containing polymer gels of the invention can be converted to porous structures of low density (foams) by removing solvent under conditions which prevent foam collapse. Foams having excellent structural integrity can be prepared by successively extracting gel, prepared as described above, with two or more liquids of progressively lower surface tension, followed by air-drying. The foams are insoluble below about 80° C. and essentially unswollen by solvents in which component enantiomers readily dissolve.

The following examples are presented to illustrate but not to restrict the present invention. Parts and percentages are by weight and temperatures are in degrees Celsius unless otherwise specified. Thermal transitions in the exemplified compositions were determined by differential scanning calorimetry (DSC). Weight- and number-average molecular weights ($\overline{M}_w$ and $\overline{M}_n$) were determined by gel permeation chromatography (GPC). Polymer polydispersity (D) is defined by the ratio $\overline{M}_w/\overline{M}_n$. "Enantiomeric excess" (ee) is given as a percentage by the formula $$\% \ ee = 100(E1-E2)/(E1+E2)$$

where E1 and E2 are the number of moles, respectively, of the more abundant enantiomer and the opposite, less abundant enantiomer. Inherent viscosity ($\eta_{inh}$) is defined by the following equation:

$$\eta_{inh} = \ln \eta_{rel}/C$$

wherein $\eta_{rel}$ represents the relative viscosity and C represents a concentration in the range of 0.2 to 1.5 g of polymer in 100 g of solvent. The relative viscosity ($\eta_{rel}$) is determined by dividing the flow time in a capillary viscometer for a solution of concentration C by the flow time for the pure solvent, measured at 60° C. $[\alpha]_D^{25}$ represents the optical rotation of sodium D light in a solution of 1 g of polymer in 100 mL of benzene at 25° C. Tensile properties of fibers and films were measured using ASTM methods: fibers (single filaments) D-2101; films, ASTM D-882 on an Instron tester (Instron Engineering Corp., Canton, Mass.). Density was determined by means of ASTM method D-1505, except for foams; foam density was estimated by immersing a weighed portion of foam in mercury and measuring the weight of mercury displaced at 25° C., from which volume is calculated. Pore volume of foam was determined by the well-known BET (Brunauer, Emmett and Teller) nitrogen adsorption method. Pores over about 600 A in diameter are not "counted" by the BET method and are measured by the known method of mercury intrusion porosimetry; see, for example, Winslow, J. Colloid and Interface Science, 67, No. 1, 42 (1978).

The poly(R-lactide) and poly(S-lactide) used in the Examples were prepared according to the following general procedure. The monomers R-lactide and S-lactide were recrystallized from toluene and dried in vacuo before polymerization.

Approximately 372 g. of R- or S-lactide was charged to a 500 ml resin kettle fitted with a mechanical stirrer, a serum stopper, and a gas inlet through which a dry nitrogen atmosphere was maintained. The resin kettle was placed in an oil bath maintained at 200° C. and the lactide was rapidly stirred until completely melted (approx. 5 minutes). Stannous octanoate (0.160 g.) and 1-dodecanol (0.085 g.) were then added via syringe and the contents of the kettle were maintained at 200° C. for 40 minutes with constant stirring during the first 30 minutes. After 30 minutes the contents became too viscous to stir. The kettle was removed from the oil bath and allowed to cool to room temperature following which the reaction mixture was removed from the kettle and dissolved in approx. 2000 mL of methylene chloride. The resulting solution was filtered, then slowly added to a Waring blender operating at high speed and containing a volume of methanol equal to three times the volume of the methylene chloride solution. The resulting precipitated poly-S-lactide was isolated via filtration and dried overnight in vacuo at ambient temperature. The polymer exhibited an inherent viscosity of 0.977 (chloroform), a melting point of 171° C., $[\alpha]_D^{25} = -193°$, $M_w$ of 198,000 (gpc) and a density of 1.2739 g/cc. Following the above procedure, similar quantity of poly(R-lactide) was prepared which exhibited an inherent viscosity of 1.029 (chloroform), a melting point of 166° C., $[\alpha]_D^{25} = +191°$, $M_w$ of 205,000 (gpc) and a density of 1.2739 g/cc.

EXAMPLE 1

Poly(lactide) films containing varying ratios of poly-R-/poly-S segments i.e., 1/0 (Comparative), 3/1, 1/1, 1/3, 0/1 (Comparative) were prepared by dissolving 0.5 g total poly(lactide) in 50 mL methylene chloride with rapid stirring for 48 hours at room temperature. The methylene chloride was then evaporated under reduced pressure leaving a tough, transparent film in the vessel which was shown by DSC to have melting transitions at about 174° C. and 220° C. except for the film containing only one enantiomer; the latter showed only one melting transition at about 174° C. On repeated melting followed by quenching to below room temperature, the low and high-melting transitions in the mixed-enantiomer compositions shifted to lower temperature (2°–3° C. for samples heated to 240° C., 10°–15° C. for samples heated to 270° C. and more for samples melted above 270° C.), and the low-melting transition generally disappeared leaving only the high-melting transition. The results demonstrate that compositions containing poly-R segments interlocked with segments of poly-S-lactide form a new crystalline phase having a melting point about 45° C. higher than the melting point of either component.

Films prepared as above containing poly-R segments/poly-S segments ratios of 10/90 and 1/99 also exhibited two melting transitions, the lower at about 177° and the higher at about 214° and 218° C. respectively.

EXAMPLE 2

Compositions of optically active polylactides of differing molecular weight (A–H) were prepared by mixing equal volumes of 10% w/v chloroform solutions of the appropriate R- and S-lactides and then allowing the solvent to slowly evaporate at ambient temperature. DSC melting points of these materials, shown in Table 1 below, indicate that the high-melting crystalline phase can form even when the respective molecular weights of the poly-R-(Ar-HR) and poly-S-lactides (AS–HS) are unmatched.

TABLE I

| Composition | | Mw/1000 | MP (°C.) |
|---|---|---|---|
| A | R- | 231 | |
|   | S- | 232 | 225/233 |
| B | R- | 270 | |
|   | S- | 280 | 223 |
| C | R- | 133 | |
|   | S- | 113 | 233 |
| D | R- | 270 | |
|   | S- | 113 | 230 |
| E | R- | 280 | |
|   | S- | 133 | 230 |
| F | R- | 231 | |
|   | S- | 113 | 232 |
| G | R- | 133 | |
|   | S- | 232 | 230 |
|   | R- | 231 | |

TABLE I-continued

| Composition | | Mw/1000 | MP (°C.) |
|---|---|---|---|
| H | | | |
|   | S- | 280 | 220 |

EXAMPLE 3

Chloroform solutions of poly-R- and poly-S-lactide (10% w/w) were mixed at room temperature and stirred until homogeneous. The solutions were cast onto glass plates and allowed to dry for several days. The films were then annealed for 1 hour at 70° C. and cut with a razor blade into strips. The tensile properties were set forth in Table II.

TABLE II

| Composition Mole ratio poly(R-lactide) poly(S-lactide) | Stress- to-Break Kpsi(MPa/6.9) | Tensile- Modulus Kpsi(MPa/6.9) | Elongation- at-Break(%) | Toughness Kpsi(MPa/6.9) |
|---|---|---|---|---|
| Comparative 1:0 | 4.5 ± 2.0 | 265 ± 20 | 3 ± 1 | 0.1 ± 0.05 |
| 3:3 | 5.3 ± 0.2 | 281 ± 8 | 10 ± 5 | |
| 1:1 | 7.3 ± 0.9 | 340 ± 40 | 12 ± 3 | 0.6 ± 0.3 |
| Comparative 0:1 | 4.3 ± 0.2 | 259 ± 25 | 3 ± 1 | |

The stress-to break is about 60% higher for films prepared from the 50/50 composition, compared to the pure enantiomers. The tensile modulus elongation-at-break and toughness are similarly improved in the blends.

Samples of polylactide film prepared as above including the comparatives and the composition of this invention (1:1) were heated to 230° C. for 210 minutes, and the weight loss was monitored. The results which are set forth in Table III show that 1:1 films are more thermally stable than films of pure enantiomer.

TABLE III

| | | Comparatives | |
|---|---|---|---|
| Time (min) | 1:1 | 1/0 | 0/1 |
| 7 | 96.8 | 97.3 | 98.3 |
| 57 | 96.5 | 95.5 | 96.7 |
| 107 | 96.4 | 93.9 | 94.3 |
| 157 | 96.3 | 92.4 | 91.6 |
| 217 | 96.2 | 90.5 | 88.7 |

In addition to singlet loss the samples of polylactide showed some loss in weight average molecular weight after heating for 210 minutes compared to the starting polymers, with the 1:1 interlocked poly(R- and S-lactide) being the most resistant as shown in Table IV.

TABLE IV

| Sample | M_w (initial)/1000 | M_w (after)/1000 |
|---|---|---|
| 1:1 | 237 | 204 |
| 1/0 (Comparative) | 220 | 102 |
| 0/1 (Comparative) | 239 | 95 |

Polylactide films were prepared from poly-R-lactide and from a 1:1 blend of poly-R- and poly-S-lactide as described above. The latter contained a high-melting phase. Samples (200 mg) of the films were incubated at 37° C. in 45 mL of a 2M phosphate buffer solution of pH 10 and the amount of soluble lactide was periodically monitored by standard enzymatic assay (H. V. Bergmeyer, Methods of Enzymatic Analysis, 3rd edit., Verlag Chemie 6, 588 (1984)) and expressed as percent polymer converted to soluble lactide. The results are shown in Table V.

TABLE V

| | Soluble Lactide (%) | |
|---|---|---|
| Days | 1:1 | Poly(R-lactide) |
| 0 | 0.00 | 0.00 |
| 14 | 0.05 | 0.46 |
| 28 | 0.28 | 0.90 |
| 42 | 0.28 | 1.13 |
| 72 | 0.56 | 3.06 |
| 87 | 0.62 | 3.86 |
| 120 | 0.84 | 7.67 |
| 127 | 1.07 | 9.01 |
| 137 | 1.41 | 10.6 |
| 142 | 1.86 | 11.4 |
| 145 | 2.37 | 11.8 |
| 148 | 2.65 | 12.6 |

The results show that the 1:1 films containing high-melting phase are about 6 times more resistant to hydrolysis than films containing only one enantiomer.

EXAMPLE 4

Solutions of poly-R- and poly-S-lactide (10%) were mixed in equal amounts and stirred at room temperature until homogeneous. The resultant solution was charged to a syringe and then ejected through a 20 gauge needle into methanol. The polylactide formed thin fibers which were removed from the solution and dried overnight at room temperature under tension. The fibers exhibited a tenacity of 4.1 Kpsi(Mpa/6.9), an elongation of 72%, a modulus of 306 Kpsi(MPa/6.9) and a toughness of 2.7 Kpsi(MPa/6.9).

EXAMPLE 5

Samples of a poly(lactide) composition containing equal molar amounts of R- and S-enantiomers were melted on a hot bar at different temperatures and drawn into fibers. The results are shown in Table VI.

TABLE VI

| Sample | Tenacity Kpsi (MPa/6.9) | Strain-at-Maximum Draw | Modulus Kpsi (MPa/6.9) | Toughness Kpsi (MPa/6.9) | Temp. (°C.) |
|---|---|---|---|---|---|
| A | 9.6 | 37% | 366 | 2.6 | 241 |
| B | 4.5 | 2 | 138 | 0.05 | 255 |
| C | 3.0 | 6 | 247 | 0.07 | 238 |
| D | 2.3 | <1 | 298 | 0.01 | 267 |

EXAMPLE 6

A 1:1 composition of poly-R- and poly-S-lactide was prepared by mixing chloroform solutions of the pure enantiomers and precipitating the thereby interlocked polymer in methanol. The polymer was air-dried and then vacuum-dried overnight at 100° C. The polymer was formed into a plug by compression molding at 150° C. for 3 minutes at 5000 psi (34.5 MPa) and spun through a capillary (0.30 mm diameter, 0.69 mm length) at 230° C. with a spin stretch of 2X.

The as-spun fiber was drawn over a hot shoe positioned between two "Grapham" drives, and at 90° C., a maximum draw of 9.8X was obtained. Tensile properties, which varied with the thermal treatment and the draw ratio, are set forth in Table VII.

TABLE VII

| Fiber Sample | Draw Ratio and Temperature (°C.) | Tenacity (MPa) | Elongation (%) | Modulus (MPa) |
|---|---|---|---|---|
| A | As-spun | 42.8 | 1.4 | 3374 |
| B | 2 × at 75 | 146 | 54 | 4837 |
| C | 2.5 × at 75 | 214 | 97 | 4837 |
| D | 2 × at 75 then 2 × at 25 | 315 | 57 | 5175 |
| E | 4 × at 75 | 111 | 58 | 4499 |
| F | 4 × at 90 | 180 | 55 | 4727 |
| G | 9.4 × at 90 | 525 | 23 | 7424 |
| H | 9.4 × at 90, heat set at 215 | 191 | 29 | 5175 |

As-spun fibers prepared as set forth above show a glass transition (Tg) at 62° C., a crystallizing transition at 96°–100° C., and melting transitions corresponding to the low- and high-melting phases. The Tg and crystallizing transitions indicate some amorphous phase. X-ray diffraction measurements indicate both low- and high-melting phases in all of the fibers except those prepared by heat-setting at 215° C. The latter contained only high-melting crystalline phase.

EXAMPLE 7

A firm gel was obtained by mixing and dissolving equimolar amounts of solid poly-R- and poly-S-lactides in chloroform (15% w/w, total polylactide) and stirring for several hours at room temperature. The gel could be cut with a spatula into smaller pieces which did not collapse or liquify after diluting to 10% (w/w) and stirring for another 48 hours.

EXAMPLE 8

Separate solutions of 10.0 g of poly-R-lactide in 50 ml of chloroform and 10.0 g of poly-S-lactide in 50 ml of chloroform were prepared. The solutions were thoroughly mixed, sealed and allowed to stand at ambient temperature for two weeks after which the solution had set to a waxy gel which could be cut into pieces with a spatula and removed from the flask. The gel was shown to be soluble in hexafluoroisopropanol. A similar gel dissolved in 1,1,2,2-tetrachloroethane (TCE) when heated to about 140° C. and then reformed on cooling to room temperature. These tests suggest that the gels are not irreversibly cross-linked. Additional tests suggest that shear rate is important for initiating and controlling the gelling process and that the time required to set to a firm gel was varied inversely with the stirring period.

EXAMPLE 9

Separate solutions of poly-S-lactide and poly-R-lactide were prepared by mixing 30 g of TCE with 3 g of polylactide and then heating and stirring at 95° C. (9% w/w). The two solutions were cooled to room temperature, and 5 g of each solution were mixed and stirred. The solution remained fluid for at least 24 hours but turned to a solid, homogeneous gel within 48 hours.

The gel dissolved near the boiling point of TCE (149° C.) to give a visually clear solution. On cooling to 25° C., the liquid resolidified to a clear gel.

Gels of 1:1 compositions of poly-R- and poly-S-lactide were similarly prepared in dimethylformamide and N-methylpyrrolidone at polymer concentrations above about 1%.

EXAMPLE 10

Separate stock solutions of poly-R- and poly-S-lactides were prepared by dissolving 10 g polymer in 56.67 g of chloroform. The solutions were mixed in ratios (R/S) of 2:1, 1:1, 1:2 (w/w) to give 15% w/w solutions which contained 33% ee poly-R-, 0% ee, and 33% ee poly-S-lactide, respectively. The solutions were stirred for seven minutes at room temperature; gelation occurred almost immediately.

EXAMPLE 11 poly(lactide) gel was prepared from a chloroform solution (12) containing 20 g total poly(lactide) 1:1 (R/S) in 100 ml solvent according to the general procedure as described in Example 8, and extracted with carbon tetrachloride in a soxhlet apparatus for 24 hours. The solvent was then changed to 1,2-dichloro-1,1,2,2-tetrafluoroethane and extraction was continued for another 24 hours. The extracted pieces of gel were air-dried for 3 hours, and then placed under vacuum (50 torr) for 24 hours. The resulting porous, solvent-free material exhibited a surface area of 152 m$^2$/g, a pore volume of 0.42 ml/g, and an average pore diameter of 111 A as measured by BET nitrogen absorption. The maximum cell-size (SEM) and estimated density of the foam were, respectively, about 1 micron and <0.51 g/ml.

Gel prepared from chloroform solution (10%) according to the general procedure of Example 8, was successively extracted four times with carbon tetrachloride and then four times with 1,2-dichloro-1,1,2,2-tetrafluoroethane. The gel had a firm, rubbery consistency. On air-drying, substantial shrinkage occurred. The estimated density of the foam was <0.54 g/ml. BET analysis showed a narrow pore-size distribution centered near 80–90 A with 90% of the pore volume derived from pores with diameters between 40 A and 120 A. The maximum cell-size was about 0.5 micron (SEM).

This example demonstrates that the large pores (100 A to 1000 A) collapse selectively when the solvent extraction is terminated after 1,2-dichloro-1,1,2,2-tetrafluoroethane. Terminating the extraction process with a solvent of higher surface tension than 1,2-dichloro-1,1,2,2-tetrafluoroethane can shift the maximum of the pore-sizes distribution to smaller pore-size and narrow the distribution of pore-sizes about the maximum. The opposite effect is expected for solvents with surface tensions less than 1,2-dichloro-1,1,2,2-tetrafluoroethane.

The estimated density of foam prepared from 10% gel in chloroform after washing in perfluorohexane was <0.28 g/ml.

EXAMPLE 12

Gel prepared from 9% TCE solution as described in Example 9 was immersed in carbon tetrachloride and allowed to stand for 24 hours. The resultant gel was translucent, firm and rubbery. The gel was successively washed with carbon tetrachloride (4 washes), with 1,2-dichloro-1,1,2,2-tetrafluoroethane (5×) and then air-dried to constant weight. On drying, the gel shrank, indicating partial collapse of the porous structure. When the dried gel was resolvated with carbon tetrachloride it approached its original dimensions. The washing procedure was repeated with 1,2-dichloro-1,1,2,2-tetrafluoroethane, followed by perfluorohexane (2×), then air-drying to constant weight. The foam showed little visible shrinkage, had an estimated density of 0.49 g/ml, a surface area of 182 ml/g, pore volume of 1.05 ml/g, average pore diameter of 230.7 A (BET absorption), and a maximum cell-size (SEM) of about 0.75 micron.

EXAMPLE 13

Gels prepared from a 5% sulfolane solution (Example 10) were immersed in heptane (gel to heptane ratio was 1:5 w/w) for 24 hours at room temperature. One-third of the heptane was then replaced with diethyl ether and allowed to equilibrate for 24 hours. The solvent was then totally replaced with pure diethyl ether and allowed to equilibrate for 24 hours; this process was repeated 3 times. Diethyl ether was then exchanged for 1,2-dichloro-1,1,2,2-tetrafluoroethane 4 times with a 24 hour equilibration period after each exchange. Finally, 1,2-dichloro-1,1,2,2-tetrafluoroethane was exchanged for perfluorohexane 4 times, again with 24 hour equilibration periods after each exchange. When air-dried to constant weight, the solvated gel exhibited a density <0.1 g/ml. Characterization by SEM revealed an open, microcellular structure, with a maximum cell size of about 1 micron. BET analysis showed a surface area of 138.5 m$^2$/g, pore volume of 0.53 ml/g, and an average pore diameter of 151.7 A.

Very similar results were obtained when the sulfolane gel was initially immersed in hexane, pentane or cyclehexane instead of heptane.

Foams were also prepared from gels formed in trioxane, NMP and dimethylformamide. In each case, low density, highly porous structures were obtained with minimal shrinkage provided solvent extraction was terminated with a low-surface tension solvent such as perfluorohexane.

EXAMPLE 14

The polylactide gel from Example 10 (10% solution) was successively washed in carbon tetrachloride (5×), 1,2-dichloro-1,1,2,2-tetrafluoroethane (5×) and perfluorohexane (7×) following the procedure of Example 13. DSC's of the three samples (33%, ee R, 0% ee, 33% ee S) showed no Tg or crystallizing transitions, and a single melting transition at 220°–230° C. BET and mercury intrusion measurements gave the following porosity data:

TABLE VIII

| Sample (ee) | Surface Area (m$^2$/g) | Pore Volume (mL/g) | Ave. Pore Diameter (Å) | Density (g/mL) |
|---|---|---|---|---|
| 33% R | 175 | 0.42 | 96 | — |
| 0% | 187 | 0.57 | 121 | 0.23 |
| 33% S | 178 | 0.57 | 129 | 0.21 |

The extent to which chloroform solutions (10%) were stirred during gel formation has been found to influence foam porosity. Gels prepared as in Example 8 were stirred for various times then successively washed as described in Example 13, followed by air-drying. The resultant foams were characterized by BET and mercury intrusion porosimetry, with the following results:

TABLE IX

| Stirring Time (Min) | Surface Area (m$^2$/g) | Pore Volume (mL/g) | Ave. Pore Diameter (Å) | Density (g/mL) |
|---|---|---|---|---|
| 0 | 199 | 0.37 | 75 | |
| 15 | 190 | 0.65 | 137 | 0.31 |
| 30 | 198 | 0.61 | 123 | 0.24 |

TABLE IX-continued

| Stirring Time (Min) | Surface Area (m²/g) | Pore Volume (mL/g) | Ave. Pore Diameter (Å) | Density (g/mL) |
|---|---|---|---|---|
| 60 | 195 | 0.75 | 153 | |

EXAMPLE 15

To illustrate the preparation of potential artificial bone a piece of porous calcium phosphate/carbonate ceramic was immersed in a 10% chloroform solution of 1:1 poly-R- and poly-S-lactide at 85°–90° C. for 5 hours. The solution was allowed to stand overnight, and the ceramic was briefly rinsed and washed as described in Example 13, followed by air-drying. The ceramic gained about 5% in weight and about 30–40% of the ceramic voids were filled by polylactide blend. The original brittleness of the ceramic was absent, and resistance to crushing was significantly increased.

EXAMPLE 16

Indicated quantities of lactide and caprolactone, totaling 40 g in each case, were placed in heavy-walled polymerization tubes together with, in each tube, 19 mg of stannous octanoate and 13 mg of n-dodecanol. The tubes were heated to about 100° C. until the reaction mixture was molten, agitated vigorously to insure homogeneity, then submersed in a thermostated oil bath and maintained at 190° for 1 hour. The resulting copolymers were dissolved in methylene chloride and precipitated into either methanol or ether: compositions, determined by proton NMR, were as follows:

TABLE X

| Copolymer Sample | Lactide Isomer | Weight (g) | Caprolactone (g) | Non-solvent |
|---|---|---|---|---|
| A | R | 20.0 | 20.0 | Methanol |
| B | R | 32.0 | 8.0 | Ether |
| C | R | 36.0 | 4.0 | Ether |
| D | S | 20.0 | 20.0 | Methanol |
| E | S | 32.0 | 8.0 | Ether |
| F | S | 36.0 | 4.0 | Ether |

Enantiomerically opposite pairs of copolymers were blended at a 1:1 ratio by dissolving the desired weight of each copolymer in methylene chloride, stirring and precipitating in methanol. The vacuum-dried compositions had the following properties:

TABLE XI

| Example | Co-polymer | Lactide (Wt. %) | Spec. Rot. | Mw | Mn | MP | Tg | Blend MP | Blend Tg |
|---|---|---|---|---|---|---|---|---|---|
| 16-1 | A | 68.9 | 130.7 | 198 K | 130 K | 113 | 17 | | |
| | D | 67.8 | −135.9 | 221 K | 137 K | 118 | 9 | 113 166 | 24 |
| 16-2 | B | 86.5 | 172.5 | 308 K | 180 K | 144 | 49 | | |
| | F | 87.6 | −178.5 | 304 K | 186 K | 144 | 46 | 146 192 | — |
| 16-3 | C | 93.5 | 183.2 | na | na | 151 | 50 | | |
| | F | 91.5 | −179.8 | 307 K 310 K[1] | 163 K 183 K[1] | 161 | | 152 199 | — | na = not analyzed
1 = Blend

The difference in melting point (49° C.±5° C.) between the low- and high-melting forms is independent of the wt % of lactide over the range of 67–100%.

EXAMPLE 17

Compositions of poly(R-lactide) or poly(S-lactide) homopolymer with optically active lactide/caprolactone copolymer wherein the lactide content is of opposite configuration were prepared by mixing, with stirring, methylene chloride solutions of the appropriate polymers, then allowing the solvent to evaporate slowly under ambient conditions. Melting points of the resulting solvent-free blends were determined by DSC. The component polymers were selected such that the molar ratio of lactide in the copolymer to opposite-configuration lactide in the homopolymer was 1:1.

TABLE XII

| Sample | Copolymer Ratio (Lactide/Lactone) | Weight (mg) | Polylactide Type | Polylactide Weight (mg) | Blend Melting Point (°C.) |
|---|---|---|---|---|---|
| A | 69R/31 | 100 | S | 69 | 190 |
| B | 69S/31 | 100 | R | 69 | 192 |
| C | 87R/13 | 100 | S | 87 | 203 |
| D | 87S/13 | 100 | R | 87 | 208 |
| E | 95R/5 | 100 | S | 95 | 205 |
| F | 95S/5 | 100 | R | 95 | 212 |

In each case two lower melting transitions, characteristic of the copolymer and homopolymer components were observed. The results of Examples 16 and 17 indicate that the novel high-melting phase is obtained in blends of enantiomerically balanced lactide copolymers and of enantiomerically balanced lactide copolymer and lactide homopolymer.

EXAMPLE 18

Fibers of poly(JS-lactide) (A) and of a 1:1 blend of poly(R-lactide) and poly(S-lactide) (B), spun at 90° C., were heat-set under tension at 190° C. for 3 minutes. Additional fibers of the 1:1 blend, spun at 90° C., were heat-set under tension at 215° C. until only one melting point, at about 220° C., was observed (C).

Fibers A melted at about 175° C. Fibers B showed two melting points, at about 175° and about 220° C., respectively.

Each set of fibers was analyzed by X-ray diffraction. The diffraction pattern of Fibers A showed a layer line spacing of 2.793 nm, consistent with a polylactide chain helix repeating after 10 monomer units. Fibers C showed a layer line spacing of 0.815 nm, consistent with a much tighter helix repeating after 3 monomer units, and very different unit cell dimensions. Fibers B showed characteristics of both fibers A and C.

Occasionally, the concentrated poly(lactide) solutions (e.g., 15–20% w/w), and polymer isolated therefrom, prepared as described above, are somewhat yellow in color. If desired, this color can be substantially reduced by adding a 15–20% solution of poly(lactide) in chloroform to 1 L of ether, with rapid stirring whereupon the polymer is precipitated as an entangled ball of thread-like filaments which can be broken up and dispersed. For further color reduction, the dispersion can be allowed to stand overnight after adding an additional 0.5 L of ether following which the polymer is collected and dried under vacuum. Some low molecular weight polymer can also be removed by this procedure. Typical properties of the poly-R-lactide treated as described are MP=175.6° C., Mn=139,000, Mw=208,000, D=1.5; while the properties of the untreated poly-R-lactide are as given above. Typical properties of the poly(S-lactide) treated as described above are MP=174.7° C., Mn=139,000, Mw=214,000, while the properties of the untreated poly(S-lactide) are as given above.

What is claimed is:

1. A porous polymeric composition comprising segments of poly(R-lactide) interlocked with segments of poly(S-lactide).

2. The composition of claim 1 wherein the molar ratio of R-lactide units to S-lactide units is in the range of about 1:99 to 99:1.

3. The composition of claim 2 wherein the molar ratio of R-lactide units to S-lactide units is in the range of about 1:9 to 9:1.

4. The composition of claim 3 wherein the molar ratio is about 1:1.

5. The composition of claim 2 consisting essentially of segments of poly(R-lactide) and segments of poly(S-lactide), each segment having a number average molecular weight of at least about 300.

6. The composition of claim 4 consisting essentially of segments of poly(R-lactide) and segments of poly(S-lactide), each segment having a number average molecular weight of at least about 10,000.

7. The composition of claim 1 wherein at least one of the segments is part of a copolymer.

8. The composition of claim 7 wherein at least one of the poly(lactide) segments is copolymerized with at least one nonlactide comonomer.

9. The composition of claim 7 wherein the copolymer is a block copolymer.

10. The composition of claim 9 wherein the block copolymer is a thermoplastic elastomer.

11. The composition of claim 7 wherein the comonomer is epsilon-caprolactone.

12. A polymeric composition comprising segments of poly(R-lactide) and segments of poly(S-lactide), said composition melting higher than either of the segments.

13. The composition of claim 1 wherein essentially all of the interlocked segments are in the high-melting phase.

14. The composition of claim 6 wherein essentially all of the interlocked segments are in the high-melting phase.

15. The composition of claim 1 in the form of a gel.

16. The process of forming a porous structure from the gel of claim 1 comprising solvent exchange and evaporation.

* * * * *